(12) United States Patent
Ness (10) Patent No.: US 7,846,088 B2
(45) Date of Patent: Dec. 7, 2010

(54) INSTRUMENTS AND METHODS FOR ACCESSING AN ANATOMIC SPACE

(75) Inventor: Gregory O. Ness, Redmond, WA (US)

(73) Assignee: Medtronic, Inc., Minneapolis, MN (US)

( * ) Notice: Subject to any disclaimer, the term of this patent is extended or adjusted under 35 U.S.C. 154(b) by 1120 days.

(21) Appl. No.: 11/520,238

(22) Filed: Sep. 13, 2006

(65) Prior Publication Data

US 2007/0010708 A1 Jan. 11, 2007

Related U.S. Application Data (62) Division of application No. 10/777,249, filed on Feb. 12, 2004, now Pat. No. 7,186,214.

(51) Int. Cl.
*A61B 1/00* (2006.01)
*A61B 1/04* (2006.01)
*A61M 31/00* (2006.01)

(52) U.S. Cl. .................................. 600/116; 604/103.07

(58) Field of Classification Search ......... 600/115–116, 600/128, 153; 604/103.06, 103.07
See application file for complete search history.

(56) References Cited

U.S. PATENT DOCUMENTS

| | | | |
|---|---|---|---|
| 4,040,413 A | 8/1977 | Ohshiro | 128/6 |
| 4,357,946 A | 11/1982 | Dutcher et al. | |
| 4,509,514 A | 4/1985 | Brain | 128/207.15 |
| 4,779,611 A | 10/1988 | Grooters et al. | 128/4 |
| 4,991,578 A | 2/1991 | Cohen | 128/419 |
| 5,071,428 A | 12/1991 | Chin et al. | 606/184 |
| 5,108,370 A | 4/1992 | Walinsky | 604/96 |
| 5,246,014 A * | 9/1993 | Williams et al. | 607/122 |
| 5,249,574 A | 10/1993 | Bush et al. | 607/9 |
| 5,250,025 A | 10/1993 | Sosnowski et al. | 604/51 |
| 5,336,252 A * | 8/1994 | Cohen | 607/119 |
| 5,402,772 A | 4/1995 | Moll et al. | 128/20 |
| 5,464,447 A | 11/1995 | Fogarty et al. | 607/129 |
| RE35,531 E | 6/1997 | Callaghan et al. | 128/207.15 |
| 5,634,895 A | 6/1997 | Igo et al. | 604/21 |
| 5,716,392 A | 2/1998 | Bourgeois et al. | 607/132 |
| 5,827,216 A | 10/1998 | Igo et al. | 604/21 |
| 5,837,007 A | 11/1998 | Altman et al. | 604/127 |
| 5,868,770 A | 2/1999 | Rygaard | 606/167 |
| 5,875,782 A | 3/1999 | Ferrari et al. | 128/898 |
| 5,972,013 A | 10/1999 | Schmidt | 606/185 |
| 6,036,685 A | 3/2000 | Mueller | 606/15 |

(Continued)

*Primary Examiner*—Philip R Smith
(74) *Attorney, Agent, or Firm*—Mike Jaro; Jeffrey J. Hohenshell (57) ABSTRACT

An anatomic space of the body, particularly the pericardial space, is accessed in a minimally invasive manner from a skin incision by an access instrument to facilitate visualization and introduction of devices or drugs or other materials, performance of medical and surgical procedures, and introducing and fixating a cardiac lead electrode to the heart. An elongated access instrument body preferentially bends in one direction and resists bending in a transverse direction, whereby the access instrument body distal end can be directed through a path around body structures to the anatomic site by manipulation of the access instrument body proximal end portion. A distal header formed at the access instrument body distal end extends outward of the access instrument body in the transverse direction and supports an inflatable balloon surrounding a working lumen exit port that is directed toward an anatomic surface when the balloon is inflated by inflation media introduced through an inflation lumen.

20 Claims, 6 Drawing Sheets

U.S. PATENT DOCUMENTS

| | | | |
|---|---|---|---|
| 6,080,175 A | 6/2000 | Hogendijk | 606/185 |
| 6,099,498 A | 8/2000 | Addis | 604/96.01 |
| 6,156,009 A | 12/2000 | Grabek | 604/117 |
| 6,162,195 A | 12/2000 | Igo et al. | 604/164 |
| 6,206,004 B1 | 3/2001 | Schmidt et al. | 128/898 |
| 6,231,518 B1 | 5/2001 | Grabek et al. | 600/508 |
| 6,277,065 B1 * | 8/2001 | Donofrio | 600/115 |
| 6,314,963 B1 | 11/2001 | Vaska et al. | |
| 6,332,468 B1 | 12/2001 | Benetti | 128/898 |
| 6,423,051 B1 | 7/2002 | Kaplan et al. | 604/506 |
| 6,461,336 B1 | 10/2002 | Larré et al. | |
| 6,478,029 B1 * | 11/2002 | Boyd et al. | 128/898 |
| 6,592,552 B1 | 7/2003 | Schmidt | 604/164.01 |
| 7,040,322 B2 * | 5/2006 | Fortuna | 128/207.15 |
| 2003/0018236 A1 | 1/2003 | Adams | 600/128 |
| 2003/0114796 A1 | 6/2003 | Schmidt | 604/158 |
| 2003/0130571 A1 | 7/2003 | Lattouf | |
| 2003/0158464 A1 | 8/2003 | Bertolero | 600/116 |
| 2003/0212446 A1 * | 11/2003 | Kaplan et al. | 607/129 |
| 2004/0015052 A1 | 1/2004 | Barthel | 600/116 |
| 2004/0138531 A1 * | 7/2004 | Bonner et al. | 600/156 |
| 2004/0199236 A1 * | 10/2004 | Laske et al. | 607/129 |

* cited by examiner

INSTRUMENTS AND METHODS FOR ACCESSING AN ANATOMIC SPACE

REFERENCE TO RELATED APPLICATIONS

This application is a divisional of U.S. patent application Ser. No. 10/777,249 filed Feb. 12, 2004 now U.S. Pat. No. 7,186,214. Reference is hereby made to commonly assigned U.S. patent application Ser. No. 10/283,794 filed Oct. 30, 2002, for METHODS AND APPARATUS FOR ACCESSING AND STABILIZING AN AREA OF THE HEART in the names of Gary W. Guenst et al, U.S. patent application Ser. No. 10/284,771 filed Oct. 31, 2002, now U.S. Pat. No. 6,890,295, for ANATOMIC SPACE ACCESS SUCTION TOOLS AND METHODS in the names of Koen Michels et al, U.S. patent application Ser. No. 10/342,960 filed Jan. 15, 2003, now U.S. Pat. No. 6,786,898, for METHODS AND TOOLS FOR ACCESSING AN ANATOMIC SPACE in the name of Gary W. Guenst, and U.S. patent application Ser. No. 10/622,147 filed Jul. 17, 2003, now U.S. Pat. No. 6,918,908, for METHODS AND APPARATUS FOR ACCESSING AND STABILIZING AN AREA OF THE HEART in the names of Mathew D. Bonner et al.

FIELD OF THE INVENTION

The present invention pertains to instruments and methods for accessing and enlarging an anatomic space of the body and particularly for accessing the pericardial space in a minimally invasive manner in order to facilitate visualization of the pericardial space and introduction of devices or drugs or other materials and performance of medical and surgical procedures including introduction and fixation of an electrode of a cardiac lead to the heart

BACKGROUND OF THE INVENTION

The human heart wall consists of an inner layer of simple squamous epithelium, referred to as the endocardium, overlying a variably thick heart muscle or myocardium and is enveloped within a multi-layer tissue structure referred to as the pericardium. The innermost layer of the pericardium, referred to as the visceral pericardium or epicardium, clothes the myocardium. The epicardium reflects outward at the origin of the aortic arch to form an outer tissue layer, referred to as the parietal pericardium, which is spaced from and forms an enclosed sac extending around the visceral pericardium of the ventricles and atria. An outermost layer of the pericardium, referred to as the fibrous pericardium, attaches the parietal pericardium to the sternum, the great vessels and the diaphragm so that the heart is confined within the middle mediastinum. Normally, the visceral pericardium and parietal pericardium lie in close contact with each other and are separated only by a thin layer of a serous pericardial fluid that enables friction free movement of the heart within the sac. The space (really more of a potential space) between the visceral and parietal pericardia is referred to as the pericardial space. In common parlance, the visceral pericardium is usually referred to as the epicardium, and epicardium will be used hereafter. Similarly, the parietal pericardium is usually referred to as the pericardium, and pericardium will be used hereafter in reference to parietal pericardium.

It is frequently medically necessary to access the pericardial space to treat an injury, infection, disease or defect of the heart, e.g., an occluded coronary artery, a defective heart valve, aberrant electrical pathways causing tachyarrhythmias, and bacterial infections, or to provide cardiac resynchronization therapy, or to place epicardial pacing or cardioversion/defibrillation electrodes against the epicardium or into the myocardium at selected sites. It is necessary in these procedures to surgically expose and cut through the pericardium to obtain access to the pericardial space.

Highly invasive surgical techniques, referred to as a median sternotomy (open-chest surgical exposure) or a thoracotomy, have been typically employed to provide the surgeon access to the pericardial space and the heart. A median sternotomy incision begins just below the sternal notch and extends slightly below the xiphoid process. A sternal retractor is used to separate the sternal edges for optimal exposure of the heart. Hemostasis of the sternal edges is typically obtained using electrocautery with a ball-tip electrode and a thin layer of bone wax.

The open chest procedure involves making a 20 to 25 cm incision in the chest of the patient, severing the sternum and cutting and peeling back various layers of tissue in order to give access to the heart and arterial sources. As a result, these operations typically require large numbers of sutures or staples to close the incision and 5 to 10 wire twisted loops to keep the severed sternum together. Such surgery often carries additional complications such as instability of the sternum, post-operative bleeding, and mediastinal infection. The thoracic muscle and ribs are also severely traumatized, and the healing process results in an unattractive scar. Post-operatively, most patients endure significant pain and must forego work or strenuous activity for a long recovery period.

Many minimally invasive surgical techniques and devices have been introduced In order to reduce the risk of morbidity, expense, trauma, patient mortality, infection, and other complications associated with open-chest cardiac surgery. Less traumatic limited open chest techniques using an abdominal (subxiphoid) approach or, alternatively, a "Chamberlain" incision (an approximately 8 cm incision at the sternocostal junction), have been developed to lessen the operating area and the associated complications. In recent years, a growing number of surgeons have begun performing coronary artery bypass graft (CABG) procedures using minimally invasive direct coronary artery bypass grafting (MIDCAB) surgical techniques and devices. Using the MIDCAB method, the heart typically is accessed through a mini-thoracotomy (i.e., a 6 to 8 cm incision in the patient's chest) that avoids the sternal splitting incision of conventional cardiac surgery. A MIDCAB technique for performing a CABG procedure is described in U.S. Pat. No. 5,875,782, for example.

Other minimally invasive, percutaneous, coronary surgical procedures have been advanced that employ multiple small trans-thoracic incisions to and through the pericardium, instruments advanced through ports inserted in the incisions, and a thoracoscope to view the accessed cardiac site while the procedure is performed as shown, for example, in U.S. Pat. Nos. 6,332,468, 5,464,447, and 5,716,392. Surgical trocars having a diameter of about 3 mm to 15 mm are fitted into lumens of tubular trocar sleeves, cannulae or ports, and the assemblies are inserted into skin incisions. The trocar tip is advanced to puncture the abdomen or chest to reach the pericardium, and the trocar is then withdrawn leaving the sleeve or port in place. Surgical instruments and other devices such as fiber optic thoracoscopes can be inserted into the body cavity through the sleeve or port lumens. As stated in the '468 patent, instruments advanced through trocars can include electrosurgical tools, graspers, forceps, scalpels, electrocauteries, clip appliers, scissors, etc. The straight, stiff, cannular, instruments requires use of inherently difficult techniques including rotation of the heart and sometimes deflation of either lung in order to reach the posterior cardiac surfaces.

Therefore, much effort has been expended to develop medical devices and techniques to access the pericardial space employing minimally invasive percutaneous procedures. One difficulty has been that normally the pericardial space is so small or thin that it is difficult to penetrate the pericardium using miniaturized instruments capable of being introduced through a port to the site without also puncturing the underling epicardium and thereby, damaging the myocardium or a coronary vessel. Proliferative adhesions occur between the pericardium and the epicardium in diseased hearts and hamper access to the pericardial space employing such minimally invasive percutaneous procedures. The simple percutaneous approach can be used to penetrate the pericardium to drain a large pericardial effusion, i.e., an accumulation of too much fluid in the pericardial space that widens the pericardial space. A spinal needle (18-20 gauge) and stylet occluding the needle lumen are advanced incrementally in a superior/posterior fashion through a small (2-4 mm) cutaneous incision between the xiphoid and costal cartilage. Periodically, the stylet is removed, and fluid aspiration is attempted through the needle lumen. The advancement is halted when fluid is successfully aspirated, and the pericardial effusion is then relieved.

Methods and apparatus for accessing the pericardial space for the insertion of implantable defibrillation leads are disclosed in U.S. Pat. Nos. 5,071,428 and 6,156,009, wherein a forceps device is used to grip the pericardium and pull it outward to form a "tent". In the '428 patent, a scissors or scalpel is introduced to cut the pericardium (pericardiotomy) under direct vision through a subxiphoid surgical incision. The forceps device disclosed in the '009 patent incorporates a mechanism for introducing electrical leads or guidewires through the outwardly displaced pericardium. Further methods and apparatus for accessing the pericardial space for the insertion of devices or drugs are disclosed in U.S. Pat. No. 6,423,051, wherein an access tube having a device access lumen is provided with a plurality of hooks in the tube distal end that can be used to hook into the pericardium to enable the lifting and "tenting" of the pericardium. A cutting instrument or sharpened tip guidewire or the like can be advanced through the device access lumen to perforate the pericardium.

Other methods and apparatus that are introduced through percutaneously placed ports or directly through small transthoracic incisions for accessing the pericardial space employ suction devices to grip the pericardium or epicardium as disclosed, for example, in U.S. Pat. Nos. 4,991,578, 5,336,252, 5,827,216, 5,868,770, 5,972,013, 6,080,175, 6,206,004, and 6,231,518 and the above-referenced '948 patent. The suction devices are configured like a catheter or tube having a single suction tool lumen and typically having a further instrument delivery lumen. The suction tool lumen terminates in a single suction tool lumen end opening through the device distal end in the '578, '252, '175, '770, and '013 patents and through the device sidewall in the '216 and '518 patents. Certain of these patents recite that the applied suction draws a "bleb," i.e., a locally expanded region of the pericardium, into the suction tool lumen or a suction chamber at the device distal end. A needle can then be advanced into the bleb and used to draw off fluids or deliver drugs into the pericardial space, or the like. In addition, it is suggested in these patents that treatment devices including catheters, guidewires, and electrodes, e.g., defibrillation electrodes, can be advanced into the pericardial space through a device introduction lumen for a variety of reasons. Although theoretically plausible, the ability to reliably maintain a vacuum seal against the pericardium when such treatment devices are advanced can be problematic. Certain of these patents also disclose use of one or more expandable member or balloon introduced into the anatomic space, e.g., the pericardial space between the epicardium and the pericardium, wherein the expandable member is introduced into the anatomic space in a deflated state. The balloon or balloons are expanded in the pericardial space to dilate or retract the pericardial space to form a procedural field for the duration of the procedure, and then deflated to enable retraction from the pericardial space and the body.

Introduction and visualization catheters including endoscopes and device or fluid delivery catheters that incorporate one or more distal circumferential balloon in the manner of a Foley catheter that inflates around the circumference of the catheter distal end to lodge the catheter body distal end within an anatomic space or chamber of the heart or other body organ are well known in the art as exemplified by U.S. Pat. Nos. 4,040,413, 4,779,611, 5,250,025, and 6,099,498, for example. Circumferential balloon catheters that are introduced via a surgical incision through the pericardium into the pericardial space are disclosed in the above-referenced '252 patent and in U.S. Patent Application Publication US 2003/0158464. The inflated circumferential balloon (or balloons) retain the distal end of the balloon catheter introduced through the pericardial incision within the pericardial space while a cardiac lead is introduced into the pericardial space and affixed to the epicardium.

Other balloon catheters that have a shaped bag or balloon or other expandable member at the distal end of the catheter body are disclosed in U.S. Pat. Nos. 5,402,772, 5,634,895, and 6,231,518, for example. Generally speaking, the bag or balloon or inflatable member is shaped to inflate to a greater expanded dimension in one direction extending laterally of the axis of the catheter body and to a lesser expanded dimension in the transverse direction extending laterally to the axis of the catheter body.

For example, a balloon catheter is disclosed in the above-referenced '518 patent that expands in the shape of a doughnut that is sandwiched between the pericardium and epicardium resulting in an open center that a drug or other material can be dispensed into to deliver the drug or material to a localized region of the epicardium.

A further drug delivery catheter adapted to be introduced into and inflated in the pericardial space is disclosed in the above-referenced '895 patent wherein a gaseous drug is pumped into a permeable balloon and is eluted through the wall of the permeable balloon applied against the epicardium and pericardium or wherein an iontophoretic delivery mechanism is employed to deliver drugs.

A number of inflatable retraction devices are disclosed in the above-referenced '772 for introduction into and expansion of various anatomic spaces. A set of tools and a complex procedure are employed to maintain the expansion while creating "windows" of the inflated retraction devices to pass other instruments through. The cage struts are inflated to enable selective expansion of the retraction device from a collapsed state into a polyhedral shape and deflated to enable contraction of the retraction device back into a collapsed state. Inelastic sheet panels extend between the cage struts, and other instruments are passed through windows formed through opposed sheets.

It would be desirable to provide additional and improved methods and apparatus that provide minimally invasive access to an anatomic space of a patient's body, particularly a patient's pericardial space to facilitate visualization of the pericardial space and introduction of devices or drugs or other materials and performance of medical and surgical procedures.

SUMMARY OF THE INVENTION

The present invention is preferably embodied in an access instrument and method of use for accessing an anatomic space between anatomic surfaces in a minimally invasive surgical procedure for any of these uses. For example, the access instrument is capable of introducing one of a visualization instrument through the working lumen to visualize the anatomic space and the first anatomic surface to select a site of the first anatomic surface, a medical instrument for performing a medical procedure, an implantable medical device, and a therapeutic drug or diagnostic agent into the anatomic space.

The access instrument comprises an elongated instrument body enclosing inflation and working lumens, and optionally including an illumination light pipe, and a distal header adapted to enlarge the anatomic space. The working lumen terminates at a working lumen exit port in the header and is employed in the introduction of other devices or drugs or materials of the types described above into the anatomic space. The elongated instrument body is shaped to preferentially bend in one direction and to resist bending in a transverse direction, whereby the instrument body distal end can be directed through a path around body structures from a surgical skin incision to the anatomic site by manipulation of the instrument body proximal end portion remaining outside of the skin incision. The distal header formed at the instrument body distal end extends outward of the instrument body in the transverse direction and supports an inflatable balloon surrounding the working lumen exit port that is directed toward an anatomic surface when the balloon is inflated by inflation media introduced through the inflation lumen.

In a preferred embodiment, the elongated instrument body is formed of an elastomer extending between the instrument body proximal end and the instrument body distal end, the elongated instrument body having a instrument body axis, a instrument body width in a width direction with respect to the instrument body axis, and a instrument body thickness in a thickness direction substantially orthogonal to the width direction. The instrument body width exceeds the instrument body thickness enabling bending of the instrument body in the thickness direction and resisting bending of the instrument body in the width direction. The distal header coupled to the instrument body distal end comprises a header body enclosing a lumen elbow that extends through a 90° bend from the distal end of the instrument body working lumen and a plate extending laterally of the instrument body axis in the width direction to a plate rim. The plate has a first plate side bounded by the plate rim, and the working lumen exit port of the distal header lumen is in the first plate side. The inflatable balloon is mounted to the plate substantially surrounding the working lumen exit port. The plate rim is relatively blunt and substantially atraumatic when applied against body tissue, but the plate rim possesses sufficient rigidity to maintain the plate shape and to function as an obdurator or tunneling instrument when advanced into an anatomic space to separate tissue layers and anatomic surfaces.

In a further preferred embodiment, the balloon is formed of distal and proximal balloon segments that can be selectively separately inflated and deflated. For example, the proximal balloon segment can be inflated while the distal balloon segment is deflated to provide a distal opening facilitating the introduction of other medical devices or drugs or diagnostic agents or materials of the types described above into the anatomic space.

In a preferred use, the distal header of the access instrument is preferably inserted through a minimal surgical incision through a patient's skin and subcutaneous tissues including an incision through the pericardium to access the pericardial space between the epicardium and the pericardium. The instrument body is manipulated from outside the skin incision to separate the pericardium from the epicardium and advance the distal header through the expanded pericardial space to a desired epicardial surface site.

During such advancement, the deflated balloon and first plate side are disposed facing toward the epicardium, and the instrument body bends readily in the thickness direction. Periodically during advancement, the balloon may be inflated to separate the pericardium and the epicardium and again deflated to enable further advancement. Instruments for visualizing the epicardium may be advanced through the working lumen and out of the working lumen exit port to inspect the epicardium and locate a desired anatomic site, e.g., a cardiac blood vessel or a space between cardiac blood vessels, depending upon the procedure to be undertaken. The anatomic site may be continuously illuminated by light transmitted through a light pipe of the instrument body and emitted by a distal light emitter.

The balloon is inflated at the desired anatomic site to create a working space between the working lumen exit port and the epicardium. A wide variety of procedures to be performed in the pericardial space, including fluid withdrawal, drug delivery, diagnostic and therapeutic electrophysiology procedures, pacemaker lead implantation, defibrillator lead placement, transmyocardial revascularization, transmyocardial revascularization with drug delivery, placement of the left ventricular assist devices, placement of the arterial bypass graphs, in situ bypass, i.e., coronary artery-venous fistulae, placement of drug/biologics/cell therapy delivery depots, closure of the left arterial appendage, and the like.

The methods and instruments of the present invention are suitable for accessing an anatomic space, particularly the pericardial space, through a wide variety of minimally invasive approaches, including at least intercostal/transthoracic and subxiphoid approaches, and the like.

This summary of the invention has been presented here simply to point out some of the ways that the invention overcomes difficulties presented in the prior art and to distinguish the invention from the prior art and is not intended to operate in any manner as a limitation on the interpretation of claims that are presented initially in the patent application and that are ultimately granted.

BRIEF DESCRIPTION OF THE DRAWINGS

These and other advantages and features of the present invention will be more readily understood from the following detailed description of the preferred embodiments thereof, when considered in conjunction with the drawings, in which like reference numerals indicate identical structures throughout the several views, and wherein.

The drawing figures are not necessarily to scale.

DETAILED DESCRIPTION OF THE PREFERRED EMBODIMENTS OF THE INVENTION

In the following detailed description, references are made to illustrative embodiments for carrying out the invention, particularly for entering the pericardium to access pericardial space and enlarge a working space over the epicardium of the heart in a minimally invasive manner in order to visualize the epicardial space and to introduce medical instruments, drugs, materials and to permanently implant medical devices, particularly to introduce and fix an electrode of a cardiac lead to the heart.

In a first preferred embodiment illustrated in FIGS. 1-7, the access instrument 10 comprises an elongated access instrument body 12 coupled to a distal header 20 adapted to be advanced to a site in the body, particularly a site in the pericardial space.

Figure 1:
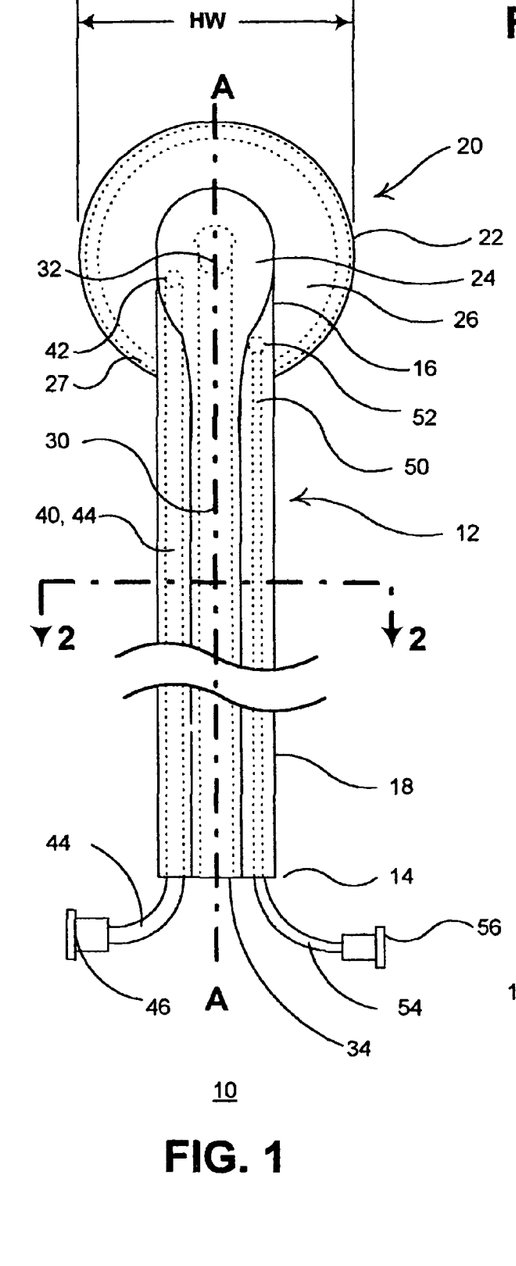
FIG. 1 is a top plan view of a first preferred embodiment of an access instrument of the present invention including an elongated instrument body and a distal header with a distal balloon inflated.
Figure 2:
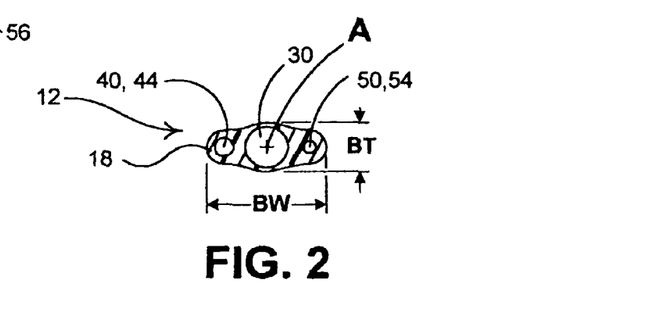
FIG. 2 is a cross-section view taken along lines 2-2 of FIG. 1 of the instrument body showing the width and thickness dimensions, inflation and working lumens, and a light pipe.

The access instrument body 12 is formed of an elastomer, e.g., silicone rubber or polyurethane or the like, having an instrument body length extending between the instrument body proximal end 14 and the instrument body distal end 16. Referring to FIGS. 1 and 2, the elongated access instrument body 12 has an instrument body axis along line A-A, a maximum instrument body width BW in a width direction with respect to the instrument body axis A-A, and a maximum instrument body thickness BT in a thickness direction with respect to the instrument body axis A-A that is substantially orthogonal to the width direction. The instrument body cross-section can shaped be substantially as depicted in FIG. 2 with somewhat convex sides or may have flattened sides and be substantially rectangular.

Figure 5:
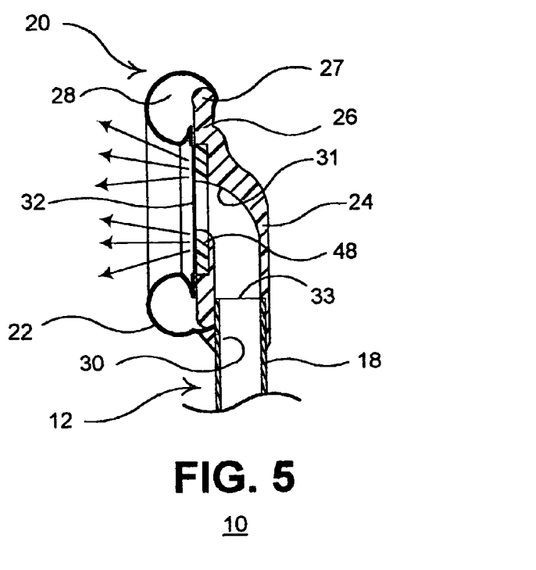
FIG. 5 is a cross-section view taken along lines 5-5 of FIG. 3 illustrating the distal head structure of the access instrument with the distal balloon inflated.
Figure 6:
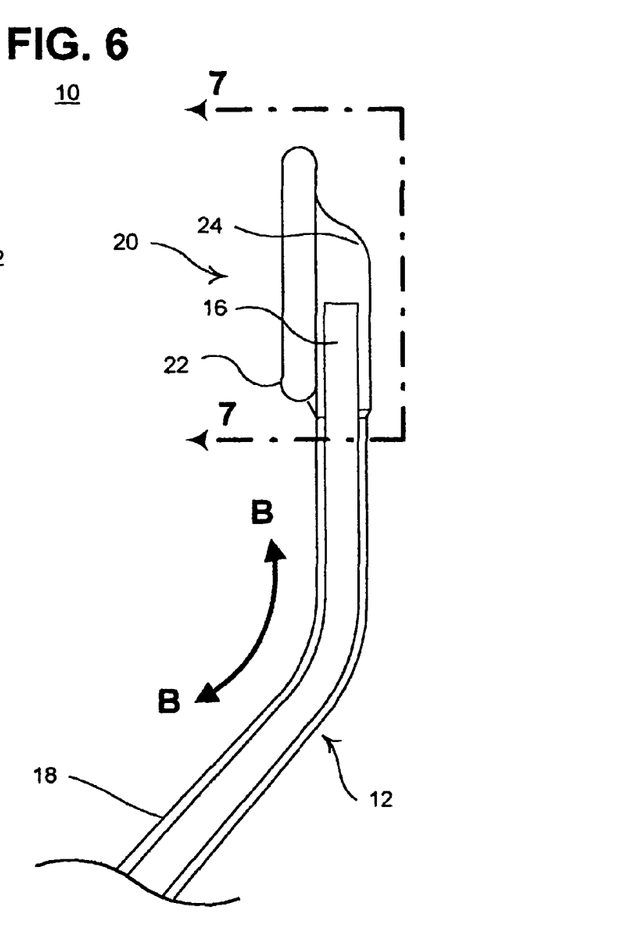
FIG. 6 is a side plan view of a distal segment of the access instrument of FIG. 1 with the distal balloon deflated and a bend induced in the thickness direction of the instrument body.
Figure 7:
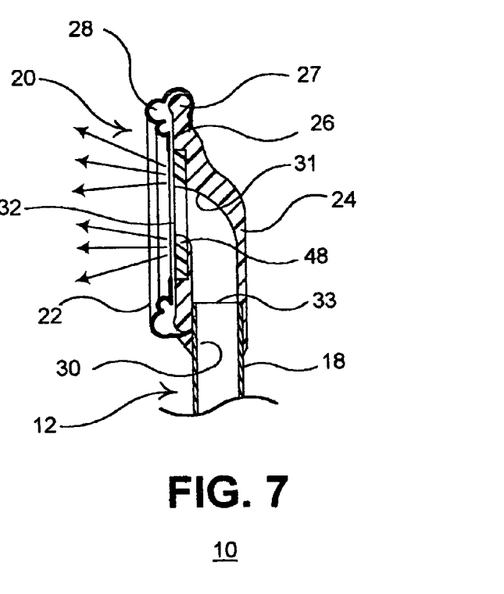
FIG. 7 is a cross-section view taken along lines 7-7 of FIG. 6 illustrating the distal head structure of the access instrument with the distal balloon deflated.
Figure 8:
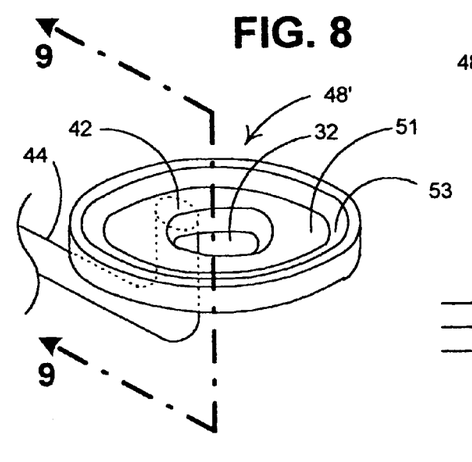
FIG. 8 is a perspective view of an alternatively shaped light ring of the distal header coupled to the distal end of the light pipe.
Figure 9:
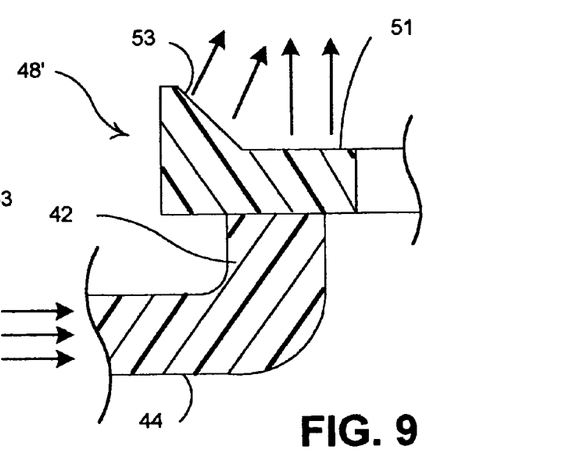
FIG. 9 is a cross-section view taken along lines 9-9 of FIG. 8 of the alternatively shaped light ring of the distal header coupled to the distal end of the light pipe.

The access instrument body 12 encloses a central working lumen 30 extending from a proximal working lumen end opening 34 shown in FIG. 1 to a distal lumen end opening 33 shown in FIGS. 5 and 7. The central working lumen 30 is preferably axially aligned with the instrument body axis A-A and may be formed during molding of the instrument body or by molding of the instrument body material about a separate, thin-walled, flexible plastic liner or sleeve. The working lumen 30 is employed in the introduction of other devices or drugs or materials of the types described above into the anatomic space.

The access instrument body 12 also encloses an inflation lumen 50 depicted in FIGS. 1 and 2 that extends alongside the working lumen 30 in parallel with instrument body axis A-A between the instrument body proximal and distal ends 14 and 16. Preferably, a length of tubing 54, shown in FIG. 1, extends from an inflation fitting 56 to the instrument body proximal end 14 and then through the inflation lumen 50 to a distal inflation tubing exit port within the distal header 20. The inflation fitting 56 is adapted to be coupled to an inflation source of a fluid or gaseous inflation media through the inflation lumen 50 from the instrument body proximal end 14 to the distal inflation port.

The access instrument body 12 also optionally comprises a light pipe lumen 40 depicted in FIGS. 1 and 2 that extends alongside the working lumen 30 in parallel with the instrument body axis A-A between the instrument body proximal and distal ends 14 and 16. An elongated, flexible, plastic, illumination light pipe 44 that extends from a proximal light pipe fitting 46 is fitted through the light pipe lumen 40 and is joined with a distal illuminating component of the distal header 20 as described further below. Alternatively, the light pipe 44 may be embedded within the access instrument body 12 as the access instrument body 12 is formed in a molding process.

The distal header 20 is formed of a header body 24 joined to the instrument body distal end 16 and a header plate 26 that extends away from the header body 24 both distally and in the instrument body width direction. The substantially circular or oval plate 26 extends laterally of the instrument body axis A-A in the width direction to a plate rim 27, thereby defining a plate width PW exceeding the maximum instrument body width BW as shown in FIG. 1. The plate 26 therefore has first and second opposed plate sides joined at the plate rim 27 and at a substantially central working lumen exit port 32. The second plate side is joined with the header body 24 as shown in FIGS. 5 and 7.

As shown in FIGS. 5 and 7, the header body 24 also encloses a working lumen elbow 31 that extends through a 90° bend from the distal end 33 of working lumen 30 to the working lumen exit port 32. The diameter of the working lumen elbow 31 may be flared somewhat between the joinder with the working lumen distal end 33 and the working lumen exit port 32 to facilitate deflection of the distal end of an instrument or medical device introduced through the working lumen through substantially 90°.

The plate 26 supports an inflatable balloon 22 that is adhered to the second plate side and extends over the plate rim 27 and is adhered to the first plate side in a narrow adhesion band extending around the working lumen exit port 32. The inflatable balloon 22 is not adhered to the plate 26 in an inflation space 28 between the adhesion band and the plate rim 27.

Figure 3:
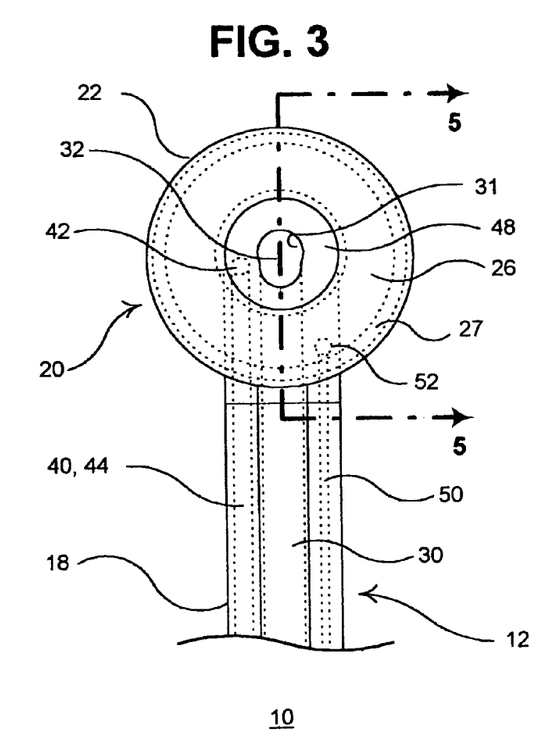
FIG. 3 is a bottom plan view of the access instrument of FIG. 1 with the balloon inflated showing the working lumen exit port.
Figure 4:
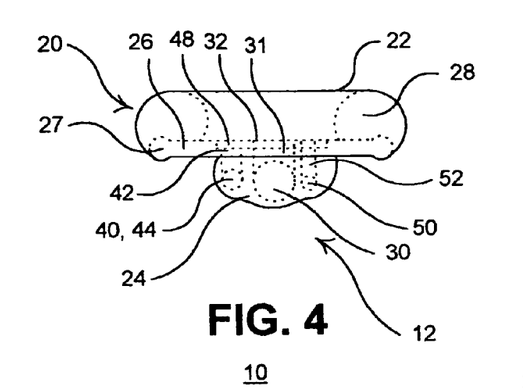
FIG. 4 is an end view of the access instrument of FIG. 3.

As shown in FIGS. 1, 3 and 4, an inflation port 52 extends from the first side of plate 26 within the inflation space 28 into the header body 24 substantially at 90° to the distal end of the inflation lumen 50 when the header body 24 is joined with the instrument body distal end 16. For example, the inflation tube 54 may extend through the inflation lumen 50 with a distal end thereof terminating at the inflation port 52 or with a distal portion of the inflation tube 54 diverted in a substantially 90° bend to fit into the inflation port 52. Thus, the inflatable balloon 22 is mounted to the plate 26 substantially surrounding the working lumen exit port 32 and is inflatable by inflation media introduced through the inflation tubing 54 from the deflated state shown in FIGS. 6 and 7 to the inflated state as shown in FIGS. 3-5.

The header body 24 and header plate 26 are also optionally formed having an illumination ring 48 of a transparent glass or plastic material surrounding the working lumen exit port 32 as shown in FIGS. 5 and 7. The distal end of the illumination light pipe 44 is joined to the illumination ring 48 at light pipe distal end 42 as by use of a transparent epoxy. The joinder may be effected through a substantially 90° bend in the light pipe distal end 42 or an extension of the illumination ring 48 into the header body 24. Light that is introduced through the proximal light pipe fitting 46 is conducted through the elongated light pipe 44 and exits the illumination ring 48. The inflatable balloon 22 may substantially transparent, and the balloon adhesion band may extend over all or part of the surface of the illumination ring 48.

The plate rim 27 is relatively blunt and substantially atraumatic when applied against body tissue, but the plate rim 27 possesses sufficient rigidity to maintain the plate shape and to function as an obdurator or tunneling instrument when the header 20 is advanced into an anatomic space to separate tissue layers or anatomic surfaces. The elongated access instrument body 12 has sufficient column strength that enables the distal header 20 to be pushed when pushing force is applied to the instrument body proximal end 14. The access instrument body 12 can be bent in the thickness direction as at bend B shown, for example, in FIG. 3 but resists being bent in the transverse width direction due to its substantially strap-like cross-section shape depicted in FIG. 2. The instrument body distal end 16 and header 20 can therefore be advanced through a path within the body around body structures from a surgical skin incision to the anatomic site by manipulation of the instrument body proximal end portion 14 remaining outside of the skin incision.

An alternative light ring 48' is depicted in FIGS. 8-11 having a faceted outer surface for selectively directing light beams in the region adjacent to the balloon 22 and the working lumen exit port 32. In the illustrated embodiment, the faceted surface comprises an inner light emitting band 51 surrounding the working lumen exit port 32 and a slanted light emitting band 53 at an angle to the inner band 51. Light transmitted through the light pipe 40 and the light pipe exit port 42 is emitted from the bands 51 and 53 such that light tends to be directed beyond the rim 27. It will be understood the light emitting surface of the light ring 48' may configured having additional slanted bands or shaped as a fresnel lens to distribute light uniformly in all directions or in a favored direction, e.g., distally to the header 20 and rim 27.

Figure 10:
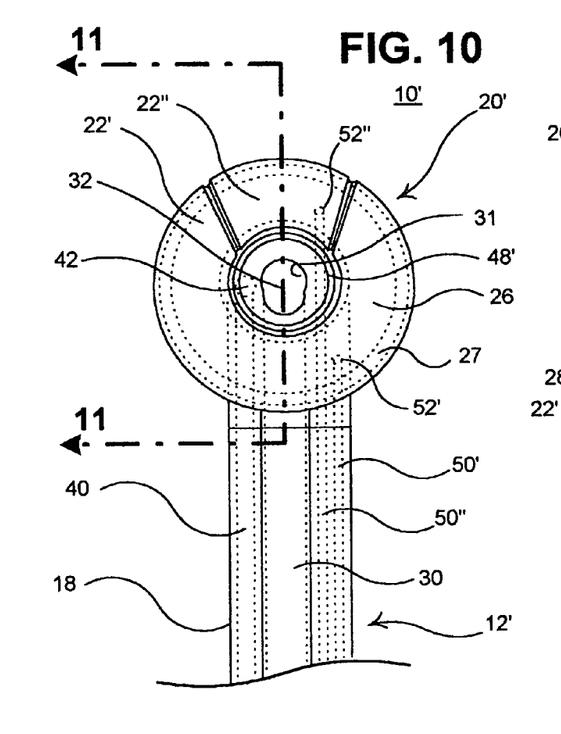
FIG. 10 is a bottom plan view of an alternative embodiment of the access instrument of the present invention incorporating the alternatively shaped light ring and proximal and distal balloons coupled to proximal and distal inflation lumens, whereby the proximal and distal balloons can be separately inflated and deflated.
Figure 11:
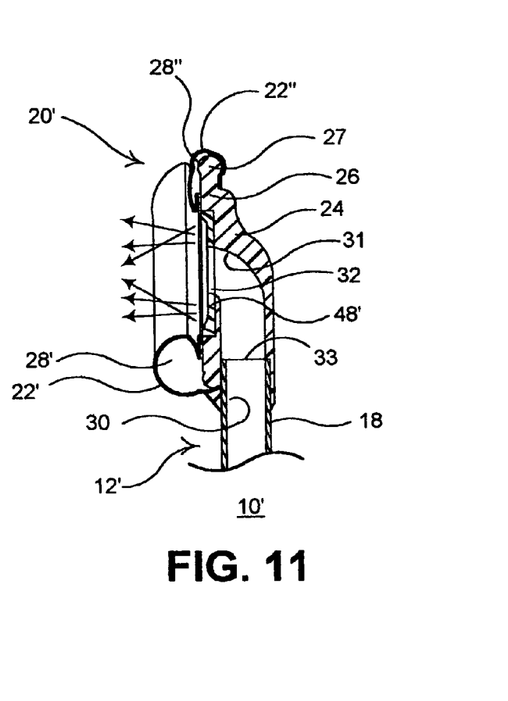
FIG. 11 is a cross-section view taken along lines 11-11 of FIG. 10 depicting the proximal balloon inflated and the distal balloon deflated.

An alternative balloon configuration is also depicted in FIGS. 10 and 11, wherein the balloon 22 is separated in a somewhat horseshoe-shaped or C-shaped, proximal balloon segment 22' and a distal balloon segment 22" supported by the plate 26. In this embodiment, the elongated access instrument body 12' comprises two inflation lumens 50' and 50" that terminate in respective inflation ports 52' and 52" open to the respective inflation spaces 28' and 28" within the respective proximal and distal balloon segments 22' and 22". The proximal balloon segment 22' and the distal balloon segment 22" can both be inflated as shown in FIG. 10, and either can be selectively inflated and deflated. In FIG. 11, the proximal balloon segment 22' is inflated to expand the anatomic space, and the distal balloon segment 22' is deflated to create a distal opening that may be useful in a variety of circumstances. For example, it may be desirable to direct a drug or other material distally through the distal opening. The distal opening can also facilitate proximal retraction of the access instrument over a medical instrument or electrical medical lead, e.g., a cardiac lead, that has been introduced through the working lumen exit port 32 as described further below. It should also be understood that the distal balloon segment 22" and associated inflation lumen 50" may be eliminated in a further variation of the preferred embodiments of the invention suitable for certain applications.

Figure 12:
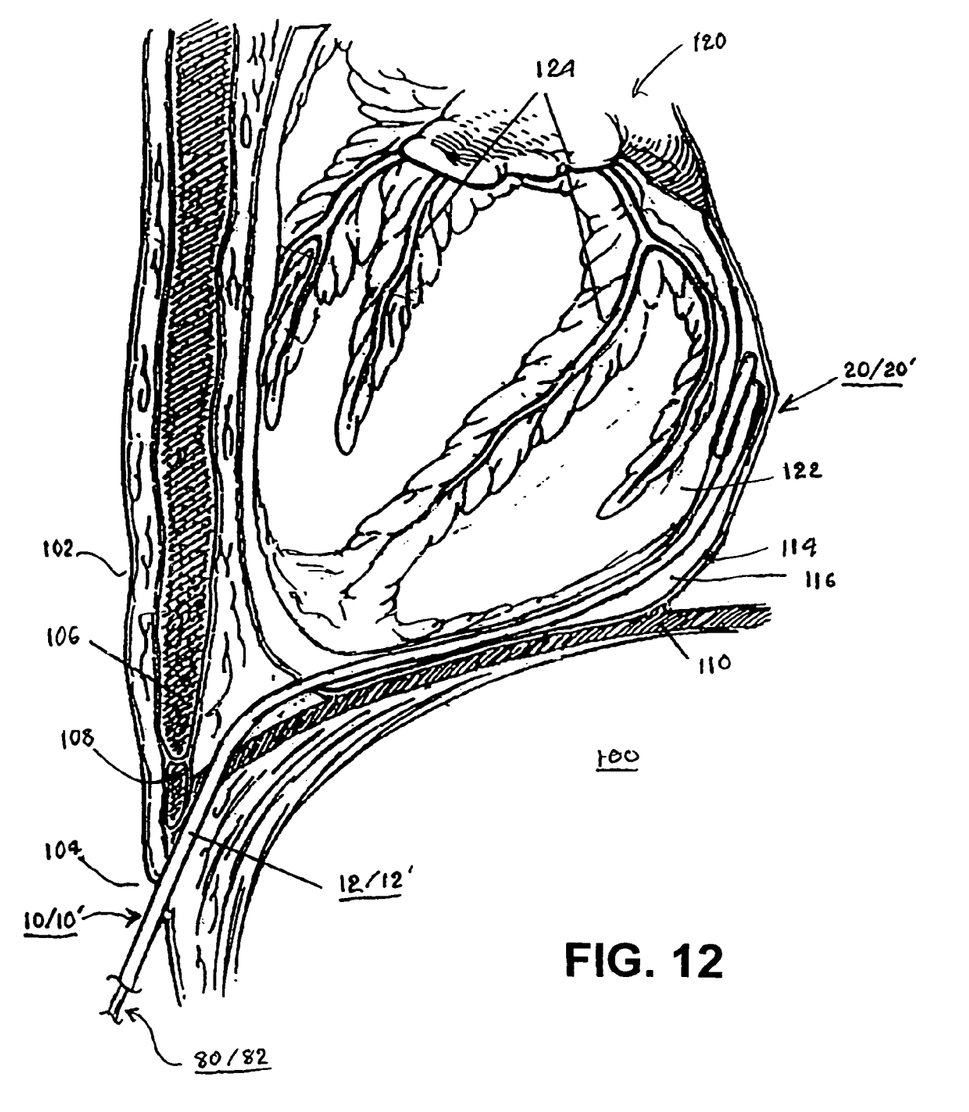
FIG. 12 is a schematic cross-section side view of a patient's thoracic region illustrating the advancement of an access instrument of the present invention with the balloon or balloons deflated to a site within the pericardial space along the left posterior heart epicardium.
Figure 13:
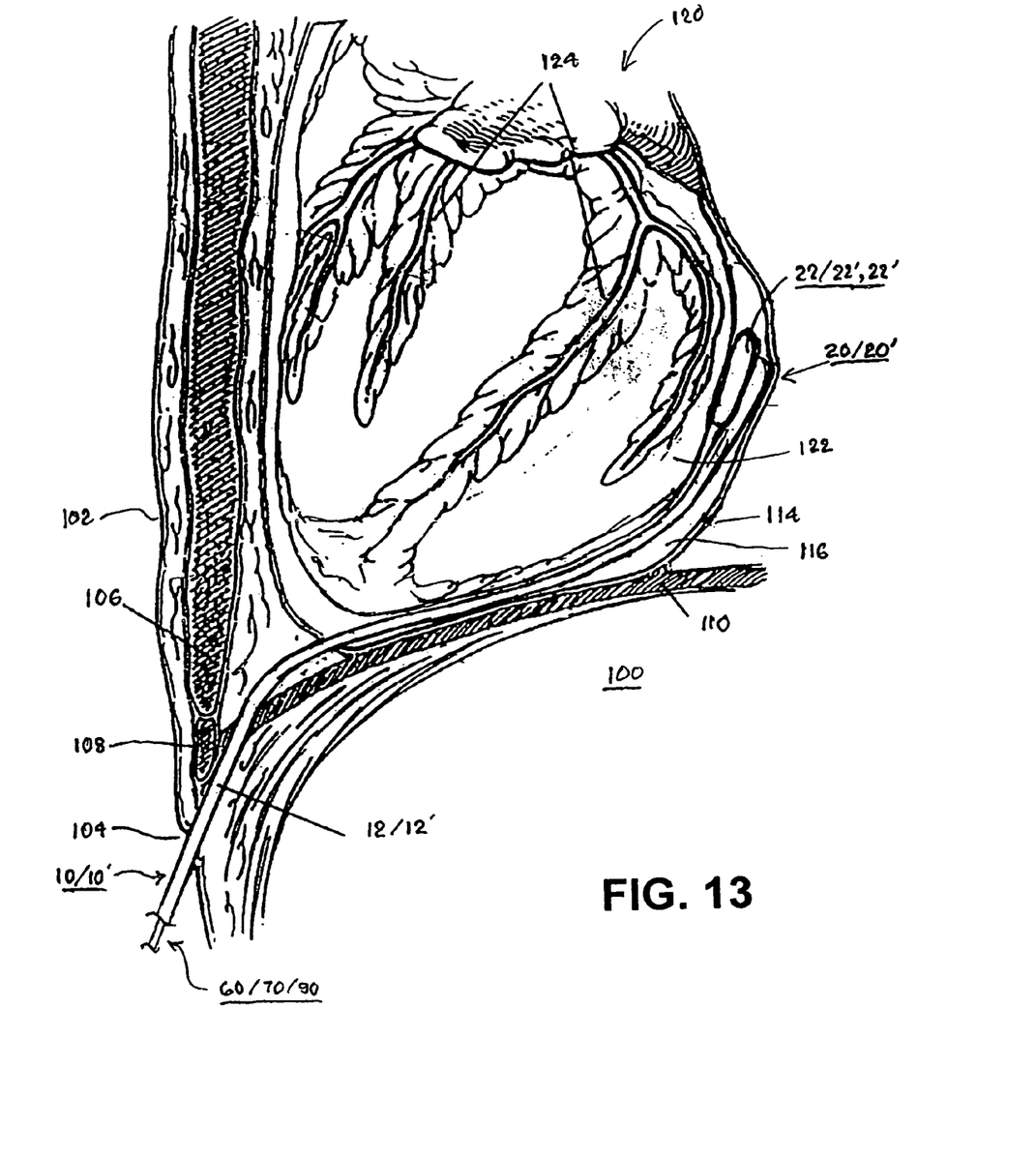
FIG. 13 is a schematic cross-section side view of a patient's thoracic region illustrating an access instrument of the present invention with the balloon or balloons inflated at the site within the pericardial space along the left posterior heart epicardium.

In a preferred use illustrated in FIGS. 12 and 13, the heart 120 is depicted in part within the pericardium 114 in a partial cross-section side view of a patient's body 100. Conventional surgical instruments are employed to make a subxiphoid incision 104 through the skin 102 below the sternum 106 and xiphoid process 108 and through subcutaneous tissue layers, the diaphragm 110 and the pericardium 114 to access the pericardial space 116. The distal header 20 or 20' of the access instrument 10 or 10' is inserted through the minimal subxiphoid surgical incision 104 and advanced into the pericardial space 116 between the epicardium 122 and the pericardium 114. The distal header 20 or 20' can advantageously be advanced to a variety of locations in the epicardial space 116 with the working lumen exit port 32 disposed toward the epicardium 122 of the right and left atria and the right and left ventricles. In FIGS. 12 and 13, the distal header 20 or 20' is depicted advanced around the apex of the heart 120 to dispose the distal header 20 or 20' at a posterior-lateral epicardial surface location along the left ventricular wall since it is often desirable to perform surgical procedures or to dispose a cardiac lead electrode.

The access instrument body 12 or 12' is manipulated from outside the skin incision 104 to separate the pericardium 114 from the epicardium 122 and to advance the distal header 20 or 20' through the expanded pericardial space 116. During such advancement, the deflated balloon 22 or 22', 22" and first plate side are disposed facing toward the epicardium 122, and the access instrument body 12 or 12' bends readily in the thickness direction. The plate ring 27 functions as a blunt dissector that separates any areas of tissue adhesion between the pericardium 114 and the epicardium 122 as the distal header 20 or 20' is advanced with the balloon 22 or 22', 22" deflated.

Although it would not necessarily be required, it may be desirable to employ a stiffening stylet 80 (FIG. 12) inserted into the working lumen 30 to stiffen and increase column strength of the elongated access instrument body 12. Similarly, it would be possible to advance the distal header 20 or 20' and access instrument body 12 or 12' over a guide wire 82 that was previously advanced through the incision 114 into the pericardial space 116 or all the way around the apex of the heart 120 to the anterior location or desired location. The proximal end of the guidewire 82 could be inserted into the working lumen exit port 32 so that the distal header 20 or 20' and access instrument body 12 or 12' can be advanced over the guide wire 82. The stylet 80 or guidewire 82 would be withdrawn proximally through the working lumen 30 after the distal header 20 or 20' is disposed at the desired site.

Figure 14:
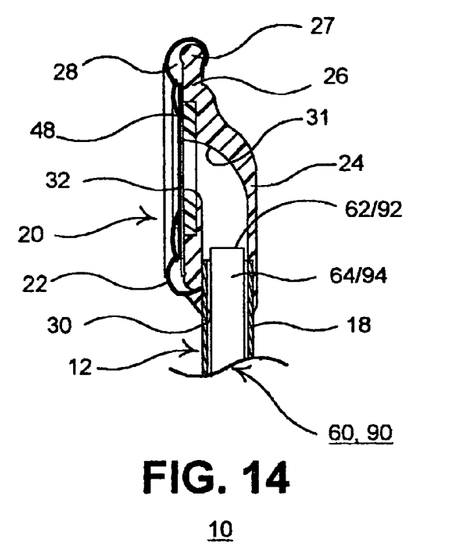
FIG. 14 is a cross-section view taken along lines 7-7 of FIG. 6 illustrating the distal head structure of the access instrument with the balloon deflated and with a catheter or other medical device or instrument located within the working lumen of the distal header in the position depicted in FIG. 12.

Periodically during advancement, the balloon 22 or 22', 22" may be inflated by inflation media introduced through the inflation lumen 50 or 50', 50" as shown in FIG. 5 or FIG. 10 to separate the pericardium 114 from the epicardium 122 and again deflated to enable further advancement of the distal header 20 or 20'. The pericardial space 114 and the epicardium 122 may be illuminated by light transmitted through light pipe 44 and emitted from the light ring 48 or 48' as shown in FIGS. 5, 7 and 11. A visualization instrument 90 (FIGS. 13-15) for visualizing the epicardium 122, e.g., any conventional, flexible, tubular endoscope coupled to or incorporating a camera and display, can be advanced through the working lumen 30 to display an image of the illuminated epicardium 122. The visualization instrument body 94 and distal end 92 are disposed in the working lumen 30 in FIG. 14. The medical instrument distal end 92 is advanced through the lumen elbow 31 and working lumen exit port 32 in FIG. 15.

In this way, cardiac blood vessels 124, illustrated in FIGS. 12 and 13 surrounded by fatty tissue on the epicardial surface, can be identified, and the distal header 20 or 20' can be disposed at an epicardial surface location between cardiac blood vessels 124. Or, a cardiac blood vessel 124 of interest can be identified, and the distal header 20 or 20' can be disposed over the blood vessel 124. The visualization instrument 90 may also stiffen the access instrument body 12 or 12' sufficiently to avoid use of a separate stiffening stylet 80. The expanded header balloon 22 or balloon segments 22' and 22" maintain the distal header 20 or 20' at the selected location, and the stiffening stylet 80 or visualization instrument 90 can be removed to enable introduction of other medical devices or drugs or materials through the working lumen 30.

A wide variety of procedures can be performed in the pericardial space 114, including fluid withdrawal, drug delivery, diagnostic and therapeutic electrophysiology procedures, pacemaker lead implantation, defibrillator lead placement, transmyocardial revascularization, transmyocardial revascularization with drug delivery, placement of the left ventricular assist devices, placement of the arterial bypass graphs, in situ bypass, i.e., coronary artery-venous fistulae, placement of drug/biologic/cell delivery depots, closure of the left arterial appendage, and the like. Medical instruments, e.g., drug delivery catheters, biological or diagnostic material delivery catheters, miniaturized biopsy forceps, devices for forming an atherectomy in a cardiac vessel, suturing tools, or the like, can be advanced through the working lumen 30 and deflected by the working lumen elbow 31 toward the epicardium 122 or target cardiac vessel 124. It will also be understood that more than one miniaturized medical instrument and/or medical device can be introduced side by side through the working lumen 30.

Figure 15:
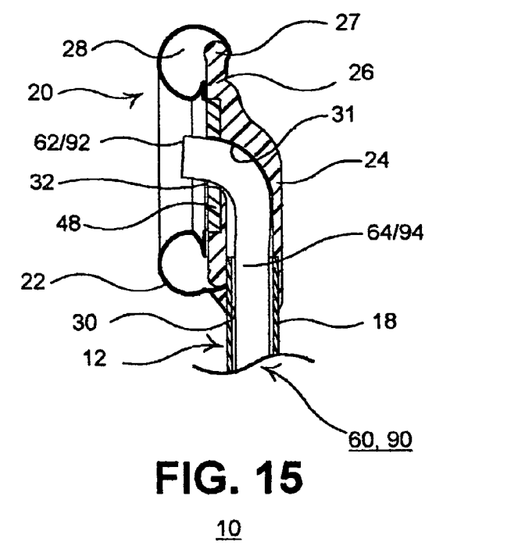
FIG. 15 is a cross-section view taken along lines 5-5 of FIG. 3 illustrating the distal head structure of the access instrument with the balloon inflated and with the distal end of the catheter or other medical device from the working lumen of the distal header to be advanced against or into proximity with the epicardium in the position depicted in FIG. 13.

Such a medical instrument 60 is also schematically depicted in FIG. 13 disposed in the working lumen 30 of the access instrument body 12 or 12'. The medical instrument 60 has an elongated medical instrument body 64 that terminates in a medical instrument distal end 62. The medical instrument distal end 62 is shown disposed in the working lumen 30 in FIG. 14 and is shown advanced through the lumen elbow 31 and working lumen exit port 32 in FIG. 15. The medical instrument distal end 62 may be advanced further from the working lumen exit port than is shown in FIG. 15.

The medical instrument body 64 can enclose one or more lumen, electrical conductor, pull wire, or other structure, and the schematically depicted medical instrument distal end 62 can comprise one or more lumen opening and/or electrode or a biopsy cutting blade or any other structure known in the art. It will be understood that the diameter of the medical instrument body 64 can be smaller than depicted in FIGS. 14 and 15 so that the access instrument 10 can be retracted proximally over the medical instrument body 64, leaving the medical instrument distal end 62 at the selected location. As noted above, it may be advantageous to employ the access instrument 10' in such a case, because the distal balloon 22" can be deflated during such retraction to lessen the friction between the medical instrument body 64 and the working lumen 30, particularly at the working lumen exit port 32 and within the working lumen elbow 31, during such retraction over the medical instrument body.

One preferred use of the access instruments 10 and 10' is to introduce a permanently implanted medical device, particularly a cardiac lead 70, e.g., a pacing lead, a cardioversion/defibrillation lead or a monitoring lead, to the epicardial surface at the site depicted in FIGS. 12 and 13 or at other selected epicardial surface sites. For example, a distal fixation mechanism 72 of a cardiac lead 70 of the type shown schematically in FIGS. 16 and 17 can be advanced through the working lumen 30 and deflected by the working lumen elbow 31 to be advanced from the working lumen exit port and fixed to the epicardium 122. It will be understood that the lead body supports at least one electrode coupled by an electrical conductor extending through the lead body 74 to a proximal electrical connector element for connection to an implantable pulse generator or monitor. The distal fixation mechanism 72 can be electrically conductive and be coupled to a lead conductor to be used as a sense electrode or pace/sense electrode as is well known in the art.

The diameter of the working lumen 30, the lumen elbow 31 and the working lumen exit port 32 can be selected to exceed the lead body diameter sufficiently to minimize friction during advancement of the cardiac lead 70 therethrough and to minimize friction on the lead body 74 during retraction of the access instrument 10' or 10' over the lead body 74. Moreover, the diameter of the working lumen 30, the lumen elbow 31 and the working lumen exit port 32 can be selected to provide sufficient clearance to enable insertion of a visualization instrument 90 therethrough alongside the lead body 74 to visualize the positioning and attachment of the distal fixation mechanism at the selected epicardial surface site.

Figure 16:
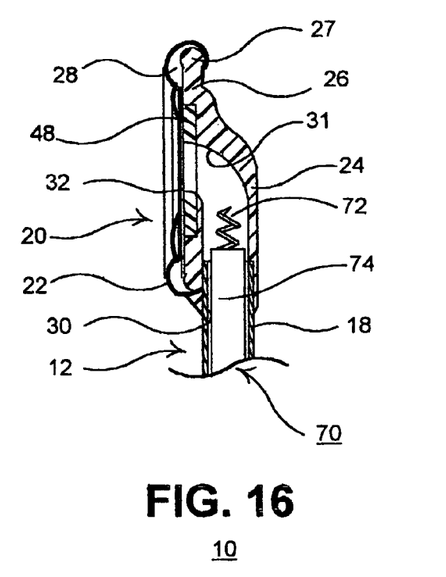
FIG. 16 is a cross-section view taken along lines 7-7 of FIG. 6 illustrating the distal head structure of the access instrument with the balloon deflated and with an electrical medical lead having an active fixation mechanism located within the working lumen of the distal header in the position depicted in FIG. 12.
Figure 17:
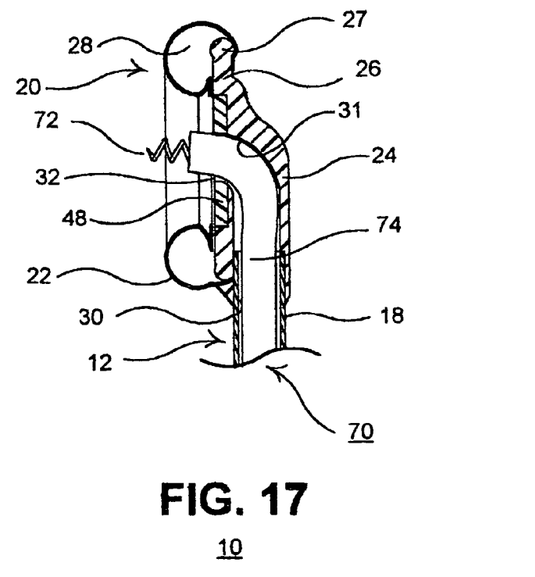
FIG. 17 is a cross-section view taken along lines 5-5 of FIG. 3 illustrating the distal head structure of the access instrument with the balloon inflated and with the active fixation mechanism advanced from the working lumen of the distal header to be advanced into the myocardium in the position depicted in FIG. 13.

Thus, it will be understood that the diameter of the lead body 74 can be smaller than depicted in FIGS. 16 and 17 so that the access instrument 10 can be retracted proximally over the lead body 74, leaving the fixation mechanism 72 attached to the myocardium at the selected epicardial surface site. As noted above, it may be advantageous to employ the access instrument 10' in such a case, because the distal balloon 22"

can be deflated during such retraction to lessen the friction between the lead body 74 and the working lumen 30, particularly at the working lumen exit port 32 and within the working lumen elbow 31, during such retraction over the medical instrument body.

The depicted distal fixation mechanism 72 is a sharpened tip helix that is adapted to be advanced from the working lumen exit port 32 by pushing the lead body 74 and screwed through the epicardium 122 into the underlying myocardium by rotating the proximal portion of the lead body 74 outside the working lumen proximal end opening 34. For example, the depicted cardiac lead 70 may comprise a screw-in pacing lead having a 0.5 mm to 3.5 mm lead body diameter.

The distal fixation mechanism 72 can take other active fixation forms including barbed hooks or loops that are inserted through the epicardium 122. Or, the cardiac lead 70 may comprise a suture-on, steroid button, pacing lead, e.g., the MEDTRONIC® Model 4968 pacing lead, having a lead distal tip larger than the diameter of the working lumen 30. In this instance, the lead body is inserted through the working lumen 30 and working lumen elbow 31 prior to advancing the assembly of the cardiac lead and access tool 10 or 10' through surgical incision 104 and into the pericardial space 116 so that the lead distal end is positioned outside the distal exit port 32 facing the epicardium 122 during such advancement. The access instrument 10' is preferably used in this procedure. The access instrument 10' and lead are then advanced as a unit through the pericardial space 116 under the guidance of a visualization catheter 90 and with the balloons 22' and 22" deflated. A manipulator instrument (that may be combined with the visualization instrument) may be used at the selected epicardial surface location to anchor the lead head to the epicardial surface. After fixation, the manipulator instrument and visualization catheter 90 can then be retracted from the working lumen 30. The distal balloon 22" can be deflated leaving the proximal balloon 22' inflated to facilitate retraction of the distal head 20' over the lead body. The proximal balloon 22' can be deflated at a selected point during retraction or left inflated throughout the retraction.

The walls of the balloon 22 and proximal and distal balloon segments 22' and 22" can be formed to be elastic or inelastic and are preferably highly transparent.

All patents and publications referenced herein are hereby incorporated by reference in their entireties.

It will be understood that certain of the above-described structures, functions and operations of the above-described preferred embodiments are not necessary to practice the present invention and are included in the description simply for completeness of an exemplary embodiment or embodiments. It will also be understood that there may be other structures, functions and operations ancillary to the typical operation of mechanical instruments that are not disclosed and are not necessary to the practice of the present invention.

In addition, it will be understood that specifically described structures, functions and operations set forth in the above-referenced patents can be practiced in conjunction with the present invention, but they are not essential to its practice.

It is therefore to be understood, that within the scope of the appended claims, the invention may be practiced otherwise than as specifically described without actually departing from the spirit and scope of the present invention.

The invention claimed is:

1. An epicardial lead access instrument for implanting an epicardial lead into the myocardium at an epicardial implantation site between the epicardium and the pericardium accessed through the thorax from a skin incision, the epicardial lead of the type having an elongated lead body extending between at least one proximal electrical connector element and a distal fixation mechanism extending from a distal electrode head, the lead body supporting at least one electrode coupled through an electrical conductor to a proximal electrical connector element, the access instrument comprising:

an elongated access instrument body formed of an elastomer extending between a access instrument body proximal end and a access instrument body distal end, the access instrument body having a access instrument body axis, a access instrument body width in a width direction with respect to the access instrument body axis, and a access instrument body thickness in a thickness direction substantially orthogonal to the width direction, the access instrument body width exceeding the access instrument body thickness enabling bending of the access instrument body in the thickness direction and resisting bending of the access instrument body in the width direction, the access instrument body enclosing an inflation lumen extending from the access instrument body proximal end through the access instrument body to an inflation lumen distal end opening and a working lumen extending from the access instrument body proximal end through the access instrument body to the access instrument body distal end dimensioned to enable passage of the lead body and distal fixation mechanism therethrough; and a distal header coupled to the access instrument body distal end comprising a header body supporting a header plate extending laterally of the access instrument body axis in the width direction to a atraumatic plate rim, the header plate having a first plate side bounded by the atraumatic plate rim, the header body enclosing a header lumen extending between the working lumen at the access instrument body distal end and a working lumen exit port through the first plate side, and an inflatable balloon mounted to the header plate adapted to be inflated by introduction of inflation media through the inflation lumen distal end opening into an inflation space between the balloon and at least a portion of the first plate side, whereby the access instrument is adapted to be advanced through the thorax from the skin incision between the epicardium and the pericardium to dispose the deflated balloon and first plate side toward the epicardium at the epicardial implantation site to enable inflation of the balloon to position the working lumen port facing toward and spaced from the epicardium allowing passage of the distal fixation mechanism from the working lumen exit port and fixation to the epicardium.

2. The access instrument of claim 1, wherein the balloon supported by the header plate substantially surrounds the working lumen exit port.

3. The access instrument of claim 1, wherein the header body and header plate extend distally from the access instrument body, whereby a distal segment of the atraumatic plate rim separates the pericardium from the epicardium as the access instrument body is advanced into the incision and into the pericardial space to a selected epicardial surface site.

4. The access instrument of claim 1, wherein:

the balloon supported by the header plate comprises a proximal balloon segment enclosing a proximal balloon segment inflation space and a distal balloon segment enclosing a distal balloon segment inflation space; and the inflation lumen of the access instrument body comprises a proximal balloon segment inflation lumen having an inflation lumen distal end opening into the proximal balloon segment inflation space and a distal balloon segment inflation lumen having an inflation lumen distal end opening into the distal balloon segment, whereby the proximal and distal balloon segments can be selectively inflated by inflation media introduced into the proximal or distal balloon segment inflation space facilitating advancement of the distal fixation mechanism into engagement with the epicardium and retraction of the access instrument over the lead body without dislodging the distal fixation mechanism.

5. The access instrument of claim 4, wherein the distal fixation mechanism comprises a fixation helix adapted to be screwed through the epicardium into the myocardium.

6. The access instrument of claim 4, wherein the cardiac lead comprises a suture-on, steroid button, pacing lead.

7. The access instrument of claim 1, wherein the access instrument body incorporates a light pipe having a light pipe proximal end adapted to be coupled to a light source external to the patient's body and extending to a light pipe distal end, and the distal header comprises a light emitter coupled to the light pipe distal end that emits light generated by the light source and conducted through the light pipe in a region adjoining the working lumen exit port to illuminate the pericardial space and the epicardial surface.

8. The access instrument of claim 7, wherein the balloon is substantially transparent to emitted light.

9. The access instrument of claim 8, wherein the light emitter comprises a light ring disposed in the first plate side in proximity to the balloon and the working lumen exit port.

10. The access instrument of claim 9, wherein the light ring is formed having a faceted outer surface for selectively directing light in the region.

11. The access instrument of claim 7, wherein the light emitter comprises a light ring disposed in the first plate side in proximity to the balloon and the working lumen exit port.

12. The access instrument of claim 11, wherein the light ring is formed having a faceted outer surface for selectively directing light in the region.

13. The access instrument of claim 7, wherein the light emitter is formed having a faceted outer surface for selectively directing light in the region.

14. The access instrument of claim 1, wherein the first plate side is substantially planar and surrounded by the atraumatic plate rim, and the first plate side is substantially in parallel to the access instrument body axis, whereby the first plate side is disposable in proximity to the epicardium when the inflatable balloon is deflated, and is disposed away from the epicardium when the inflatable balloon is inflated.

15. The access instrument of claim 14, wherein the inflation of the inflatable balloon facilitates expansion of the pericardial space, visualization of the epicardium and cardiac vessels to locate a epicardial surface site, and positioning, introduction, and fixation of the distal fixation mechanism of the cardiac lead.

16. The access instrument of claim 15, wherein the distal fixation mechanism comprises a fixation helix adapted to be screwed through the epicardium into the myocardium.

17. The access instrument of claim 15, wherein the cardiac lead comprises a suture-on, steroid button, pacing lead.

18. The access instrument of claim 1, wherein the inflation of the inflatable balloon facilitates expansion of the pericardial space, visualization of the epicardium and cardiac vessels to locate a epicardial surface site, and positioning, introduction, and fixation of the distal fixation mechanism of the cardiac lead.

19. The access instrument of claim 1, wherein the distal fixation mechanism comprises a fixation helix adapted to be screwed through the epicardium into the myocardium.

20. The access instrument of claim 1, wherein the cardiac lead comprises a suture-on, steroid button, pacing lead.

* * * * *